US012559518B2

(12) United States Patent
Xiang et al.

(10) Patent No.: US 12,559,518 B2
(45) Date of Patent: Feb. 24, 2026

(54) METHOD FOR PURIFICATION OF RECOMBINANT PROTEINS

(71) Applicant: TONGHUA ANRATE BIOPHARMACEUTICAL CO., LTD, Jilin (CN)

(72) Inventors: Wei Xiang, Jilin (CN); Zhilei Yue, Jilin (CN); Hongzhi Zhao, Jilin (CN); Congwei Shao, Jilin (CN)

(73) Assignee: TONGHUA ANRATE BIOPHARMACEUTICAL CO., LTD, Jilin (CN)

( * ) Notice: Subject to any disclaimer, the term of this patent is extended or adjusted under 35 U.S.C. 154(b) by 390 days.

(21) Appl. No.: 18/026,831

(22) PCT Filed: Dec. 8, 2020

(86) PCT No.: PCT/CN2020/134385
§ 371 (c)(1),
(2) Date: Mar. 17, 2023

(87) PCT Pub. No.: WO2022/120547
PCT Pub. Date: Jun. 16, 2022

(65) Prior Publication Data
US 2023/0331772 A1     Oct. 19, 2023

(51) Int. Cl.
*C07K 1/16*        (2006.01)
*C07K 14/535*      (2006.01)
*C07K 14/54*       (2006.01)
*C07K 14/555*      (2006.01)
*C07K 14/61*       (2006.01)
*C07K 14/765*      (2006.01)

(52) U.S. Cl.
CPC .............. *C07K 1/16* (2013.01); *C07K 14/535* (2013.01); *C07K 14/54* (2013.01); *C07K 14/555* (2013.01); *C07K 14/61* (2013.01); *C07K 14/765* (2013.01); *C07K 2319/31* (2013.01)

(58) Field of Classification Search
None
See application file for complete search history.

(56) References Cited

U.S. PATENT DOCUMENTS

| | | | | |
|---|---|---|---|---|
| 5,294,699 A | * | 3/1994 | Ohmura et al. | .............. 530/364 |
| 5,986,062 A | | 11/1999 | Ohmura et al. | |
| 6,617,133 B1 | | 9/2003 | Noda et al. | |

FOREIGN PATENT DOCUMENTS

| | | |
|---|---|---|
| CA | 2157219 | 3/1996 |
| CN | 1127299 | 7/1996 |
| CN | 1496993 | 5/2004 |
| CN | 1550504 | 12/2004 |
| CN | 1810834 | 8/2006 |
| CN | 1854155 | 11/2006 |
| CN | 1880334 | 12/2006 |
| CN | 101768206 | 7/2010 |
| CN | 102070714 | 5/2011 |
| CN | 102190722 | 9/2011 |
| CN | 102234332 | 11/2011 |
| CN | 104395338 | 3/2015 |
| CN | 110092827 | 8/2019 |
| KR | 100386762 | 12/2005 |
| RU | 2322505 | 4/2008 |
| WO | 2011064247 | 6/2011 |

OTHER PUBLICATIONS

Google Patents translation of CN-102234332 (Year: 2011).*
Li et al., A novel purification procedure for recombinant human serum albumin expressed in Pichia pastoris, Protein Expression and Purification 149 (2018) 37-4 (2018) (Year: 2018).*
"Office Action of Russia Counterpart Application", issued on Jan. 22, 2024, with English translation thereof, p. 1-p. 14.
"International Search Report (Form PCT/ISA/210) of PCT/CN2020/134385", mailed on Sep. 7, 2021, with English translation thereof, pp. 1-6.
"Office Action of Canada Counterpart Application", issued on May 30, 2024, p. 1-p. 3.
"Office Action of Russia Counterpart Application", issued on Jun. 11, 2024, with English translation thereof, p. 1-p. 9.
Wen-Ning Chua et al., "High-throughput screening and optimization of mixed-mode resins for human serum albumin separation with microtiter filter plate", Biochemical Engineering Journal, vol. 131, Dec. 2017, pp. 47-57.
Stefan Schulte, "Half-life extension through albumin fusion technologies", Thrombosis Research, vol. 124, Suppl. 2 , Dec. 2009, pp. S6-S8.
Shuqiang Zhao et al., "Extending the Serum Half-Life of G-CSF via Fusion with the Domain Ill of Human Serum Albumin", BioMed Research International, vol. 2013, Aug. 2013, pp. 1-8.

* cited by examiner

*Primary Examiner* — Robert A Wax
(74) *Attorney, Agent, or Firm* — JCIPRNET

(57) ABSTRACT

The present invention provides a method for purification of a recombinant protein, in particular to a recombinant human albumin; the method includes: (a) adding aminoguanidine and a medium-long chain fatty acid to a sample containing the recombinant protein; and (b) chromatographing the obtained sample, where the chromatography is optionally performed with a chromatographic buffer solution containing aminoguanidine.

16 Claims, 3 Drawing Sheets

1 2 3 4 5 6

1 2 3 4 5 6

1 2 3 4 5 6 7 8 9 10

METHOD FOR PURIFICATION OF RECOMBINANT PROTEINS

CROSS-REFERENCE TO RELATED APPLICATION

This application is a 371 of international application of PCT application serial no. PCT/CN2020/134385, filed on Dec. 8, 2020. The entirety of the above-mentioned patent application is hereby incorporated by reference herein and made a part of this specification.

BACKGROUND OF THE INVENTION

1. Technical Field

The present invention relates to a method for purification of a recombinant protein. More specifically, the present invention relates to a method for efficient purification of a recombinant protein from a sample containing a recombinant protein, in particular to a recombinant human albumin.

2. Background Art

Human albumin is a single-chain, non-glycosylated protein with a heart-shaped structure, and has 585 amino acids, 17 pairs of disulfide bonds, one free sulfydryl group and has a molecular weight of 66438 Daltons. The half-life of human albumin in a human body is 19-21 days. The heart-shaped structure of human albumin consists of three major structural domains and six subdomains wrapped by 17 disulfide bonds, which are loosely incorporated together by Van der Waals' force. As can be seen from its crystal structure, disulfide bridges confer stiffness to the helical spherical structure and provide sufficient flexibility, thus enabling conformational changes in the protein in response to changes of the surrounding media.

Human albumin is conventionally produced by isolation and purification from human serum, and collectively known as human serum albumin. Human blood-derived human albumin is limited in the amount of plasma sources and affected by viral contamination of plasma donors, as well as individual antibody and protein differences, making it risky in clinical use. Therefore, instructions for use of human blood albumin in many countries include a viral safety statement, for example: "standard measures taken to prevent infections resulting from the use of human blood or plasma products include blood donor selection, screening of a single blood supply or screening of the plasma pool for specific infection markers and the use of effective production procedures for inactivation/removal of viruses. Even so, the possibility of infection by an infectious agent cannot be excluded when a medicinal product prepared from blood or plasma is selected for use. This includes unknown or emerging viruses and other pathogens." Therefore, using a genetic recombination method is the best way to efficiently obtain albumin free of viral contamination.

Currently, yeast expression systems are mainly the most commonly used ways to human albumin expression by recombinant microorganisms capable of achieving large-scale production, among which the expression systems using *Saccharomyces cerevisiae* and *Pichia pastoris* are most mature. However, since human albumin is a high-volume injection, the dose per injection can be up to 5-30 g. Therefore, it is required that total residues of the host cell protein and ELISA test results for contaminants in the production process should not be greater than 1 ng/ml (200 mg/ml-rHA) per injectable dose. Regardless of the method used for producing recombinant human albumin, its immunogenicity also includes post-translational modifications of proteins, such as glycosylation, oxidation, multimerization and aggregation, and the like. Therefore, efficient and specific purification is the key process element to obtain high-purity recombinant human albumin.

Previous purification processes have used existing purification media, which are complex in process and usually fail to obtain ultra-high purity recombinant human albumin. Chinese patent application CN1127299 discloses co-heating of the fermentation broth with bacterial cells to inactivate the yeast active protease, and about 20-30% or more dimer appearing in the first step of enrichment purification of Sepharose-Streamline-SP is applied and needs to be heated to be reduced and depolymerized, and then the 45 KDa albumin fragment is removed by HIC hydrophobic chromatography, and the pigment is removed by Sepharose-DEAE chromatography. In this application, the fermentation broth and the bacterial cells are heated above 58-65° C. to inactivate proteases, resulting in cross-linking of heat shock proteins with recombinant human albumin and host protein in the yeast, making it difficult in the subsequent chromatographic purification. Meanwhile, the separation purification and running efficiency of co-flowing the bacterial cells and the fermentation broth through the Sepharose-Streamline-SP chromatography of fluidized bed is very low.

Chinese patent applications CN101768206 and CN1854155 and CN1496993 disclose the use of a highly salt-tolerant Sepharose HSL cationic medium to enrich and capture the recombinant human albumin in d the fermentation broth, followed by the use of a Sepharose phenyl HIC medium to remove albumin fragments, and then the use of a Sepharose aminobutyl anionic exchange chromatography medium to replace Sepharose DEAE to improve the yield.

Chinese patent applications CN1810834 and CN1550504 and CN1880334 disclose the use of Sepharose SP FF to capture and enrich recombinant human albumin, followed by the use of Delta blue column affinity chromatography to absorb albumin to remove the 45 KDa albumin fragments and host proteins of yeast; the disadvantages of the blue column are the ligand shedding and safety of the blue dye, and the process design of separating recombinant human albumin by affinity chromatography leads to reduced efficiency in purification. The subsequent use of the molecular sieve S-200HR is also a step to cause low purification efficiency.

The above three series of disclosed patents can effectively obtain recombinant human albumin with higher purity, but the amount of polymers generated during the capture enrichment process in the pre-purification stage is large and the polymers needs to be re-depolymerized, and the depolymerization process possibly causes mismatches and other immunogenic recombinant human albumins.

Therefore, there is a continuing demand for the methods of efficiently purifying a recombinant protein, particularly a recombinant human albumin in the field, thus reducing polymer production and inhibiting the interaction of host proteins, pigments and carbohydrates with recombinant proteins.

SUMMARY OF THE INVENTION

In one embodiment of the present invention, a method for purification of a recombinant protein is provided, particularly a recombinant human albumin, including:

(a) adding aminoguanidine and a medium-long chain fatty acid to a sample containing the recombinant protein; and (b) chromatographing the obtained sample, where the chromatography is optionally performed with a chromatographic buffer solution containing aminoguanidine.

In one embodiment of the present invention, the sample containing the recombinant protein is a fermentation supernatant. Preferably, a clear supernatant is obtained from the fermentation broth by conventional techniques such as centrifugation, solid-liquid separation, heating inactivation, hollow fiber ultrafiltration or/and deep filtration clarification and separation.

In one embodiment of the present invention, the solid-liquid separation is performed by a centrifugal machine, which may rapidly separate fermented bacterial cells from the supernatant to keep the fermentation broth consistent; after the solid-liquid separation of the fermentation broth, the fermentation supernatant may be heated within 55-68° C. in the presence of sodium octanoate and other heat stabilizers for solid-liquid separation again; then clarification is performed using a 300-500 KDa membrane package or hollow fiber with or a hollow fiber with a membrane pore size within 0.1-2 μm. The clarification treatment may be performed once before and after heating inactivation.

In another embodiment of the present invention, the aminoguanidine in the step (a) has a concentration of 2-100 mmol/g (recombinant protein), preferably the aminoguanidine has a concentration of 3-80 mmol/g (recombinant protein).

In one embodiment of the present invention, the medium-long chain fatty acid is selected from one or more of octanoic acid, capric acid, myristic acid (C14:0), palmitic acid (C16:0), stearic acid (C18:0), oleic acid (C18:1), linoleic acid (C18:2), linolenic acid (C18:3), arachidonic acid (C20:4) and a salt thereof. In one embodiment, the medium-long chain fatty acid has a concentration of 2-300 mmol/g (recombinant protein). Preferably, the medium-long chain fatty acid has a concentration of 6-150 mmol/g (recombinant protein).

In one embodiment of the present invention, the chromatography includes cation exchange chromatography and hydrophobic chromatography.

In other embodiments, the recombinant protein may also be G-CSF, GLP-1, an interferon, a growth hormone, an interleukin and analogues thereof, and fusion proteins of the above-mentioned proteins with albumin.

Unlike the prior art, the inventors of the present application unexpectedly find that several unexpected effects can be generated by adding aminoguanidine and a medium-long chain fatty acid to a sample containing recombinant human albumin, followed by cationic chromatography and hydrophobic chromatography (optionally performed with an aminoguanidine-containing chromatographic buffer solution). First, aminoguanidine can prevent and reduce the previous tendency of cation exchange medium to produce dimers, multimers and heteromers; the medium-long chain fatty acid acts as an active strong ligand to inhibit most of the host proteins, pigments and carbohydrates from interacting with albumin. Thus, embodiments of the present invention significantly reduce polymers, heteromers, pigments and host proteins prevalent in cation exchange chromatography. Second, the presence of aminoguanidine and the medium-long chain fatty acid inhibits the polymerization of mutual disulfide bonds between the recombinant albumin fragments with molecular weight of 45 KDa, thus facilitating the exposure of more hydrophobic regions of unfoldable protein fragments, allowing more thorough removal of small molecule fragments of recombinant human albumin and a large number of hydrophobic impurities by hydrophobic chromatography, as well as removing yeast pigments with strong hydrophobic structures.

In one embodiment of the present invention, aminoguanidine in a chromatographic balanced solution, a wash solution or an elution buffer solution for the cation exchange chromatography has a concentration of 1-200 mmol/L, preferably, the aminoguanidine in the chromatographic balanced solution, wash solution or elution buffer solution has a concentration of 1-150 mmol/L.

In one embodiment of the present invention, the chromatographic balanced solution and the wash solution for the cation exchange chromatography have a pH value of 4.0-6.0, preferably 4.0-5.5; the elution buffer solution has a pH value of 7.0-9.5, preferably 7.0-8.5.

In one embodiment of the present invention, the chromatographic balanced solution and the wash solution for the cation exchange chromatography have a conductivity not greater than 15 ms/cm, preferably not greater than 10 ms/cm; the elution buffer solution has a conductivity not greater than 30 ms/cm, preferably not greater than 25 ms/cm.

In one embodiment of the present invention, the chromatographic balanced solution and the wash solution for the cation exchange chromatography are phosphoric acid or acetic acid or a Tris buffer solution, preferably phosphoric acid or acetic acid buffer solution.

In one embodiment of the present invention, a medium substrate for the cation exchange chromatography is a polyacrylate substrate, a polystyrene-divinyl benzene substrate, an agarose substrate, a modified cellulose substrate.

In one embodiment of the present invention, the medium for the cation exchange chromatography is coupled with a hydrophobic cationic ligand, and the hydrophobic cationic ligand includes a highly salt-tolerant Sepharose Capto MMC.

In one embodiment of the present invention, the medium for the cation exchange chromatography is selected from a Uni-SP series, a UniGel-SP series, a NanoGel-SP series, a MonoMix-HC SP series, a MonoMix-MC SP series, a Sepharose series or Bestarose series of agarose.

In one embodiment of the present invention, a medium for the hydrophobic chromatography is hydrophilically modified agarose, polyacrylate, polystyrene-divinyl benzene substrate microspheres coupled with a hydrophobic ligand of Phenyl or Butyl series; or a medium for the hydrophobic chromatography is a hydrophilic polymethacrylate matrix coupled with a hydrophobic ligand of Phenyl or Butyl series.

In one embodiment of the present invention, the medium for the hydrophobic chromatography is selected from a UniHR Phenyl series, a NanoHR Phenyl series, a UniHR Butyl series, a NanoHR Butyl series, a MonoMix-MC Butyl series, a MonoMix-MC Phenyl series, a Sepharose series or Bestarose series of agarose.

For cation exchange chromatography and hydrophobic chromatography, a cationic ligand or a hydrophobic ligand separation medium coupled a hydrophilic surface-modified polyacrylate or polystyrene-divinyl benzene or polymethacrylate substrate microsphere is preferred.

The substrate separation medium hydrophilically modified by polyacrylate polymer microsphere employed in the present invention is further, for example, hydrophilic modified Fractogel® ion exchange of polymethacrylate, and hydrophobic substrates of affinity chromatography filler products which are manufactured by Merck Millipore, including but not limited to the following series: cationic exchange medium Fractogel® EMD $SO_3^-$ (S) Resin or Fractogel® $SO_3^-$ (strong CEX) or Fractogel® SE Hicap (strong CEX) or Eshmuno® S (strong CEX), and the like.

The present invention includes but is not limited to cationic and hydrophobic separation media hydrophilically modified after synthesis of the same substrate medium.

Preferably, the present invention applies the above Fractogel® hydrophilic modified substrate separation medium of polymethacrylate produced by Merck Millipore and the above hydrophilic modified coupling separation medium of polyacrylate or polystyrene-divinyl benzene microspheres produced by Suzhou NanoMicro Technology Co. Ltd. or Sepax Technologies, Inc.; most preferably, the above hydrophilic modified coupling separation medium of polyacrylate or polystyrene-divinylbezene microspheres produced by Suzhou NanoMicro Technology Co. Ltd. and Sepax Technologies, Inc.

The replacement of buffer solutions and concentration process among various chromatography steps of the present invention may be implemented using devices and equipment such as hollow fiber membranes and flat membrane packages with a separation pore size of 1 KDa-30 KDa molecular weight, including but not limited to using them sequentially or alternatively.

The replacement of buffer solutions among chromatography steps of the present invention can may also be performed using Sephadex G25 or Superdex G75.

Furthermore, the inventors of the present application further unexpectedly find that in the above chromatography, it is preferred to use a polyacrylate or polymethacrylate or polystyrene-divinyl benzene microsphere with a diameter of 10-150 μm; after being modified by hydrophilic coating, cationic and hydrophobic ligands are grafted, for example, a Uni-SP series, a UniGel-SP or a NanoGel-SP series, a MonoMix-HC SP or a MonoMix-MC SP series of the cation exchange medium; a UniHR Phenyl series, a NanoHR Phenyl series, a UniHR Butyl series and a NanoHR Butyl series, a MonoMix-MC Butyl series or a MonoMix-MC Phenyl series for hydrophobic chromatography. This type of separation purification media retain a certain degree of hydrophobicity of the polyacrylate or polymethacrylate or polystyrene-divinyl benzene itself or the coating thereof, thus making it easier to remove pigments and host proteins in the chromatography in combination with the recombinant human albumin containing aminoguanidine and a medium-long chain fatty acid.

In one embodiment of the present invention, the hydrophobic chromatography has a pH value of 6.0-8.5, preferably 6.5-8.0.

In one embodiment of the present invention, the hydrophobic chromatography has a conductivity not greater than 30 ms/cm, preferably not greater than 25 ms/cm.

In one embodiment of the present invention, aminoguanidine in a loading solution for the hydrophobic chromatography has a concentration of 1-100 mmol/g recombinant protein.

In one embodiment of the present invention, the aminoguanidine is in a form of salt thereof, preferably a hydrochloride thereof.

The method of the present invention is mainly applied in the pre-purification process of yeast expression fermentation supernatant, thus facilitating the process of enriching the fermentation broth and improving the purification accuracy, so as to improve efficiency, increase yield and reduce cost in the later refinement and purification.

The method of the present invention may also be applied to other processes of recombinant human albumin, including but not limited to applications in the refining process, intermediate purification process.

In some specific embodiments of the present invention, the hydrophilically modified polymeric microsphere of polyacrylate or polymethacrylate or polystyrene-divinyl benzene has a pore diameter of 300-3000 Å and a microsphere diameter of 10-150 μm.

In some specific embodiments of the present invention, 10-150 μm microspheres composed of polyacrylate or polystyrene-divinyl benzene polymer belong to high-strength polymeric materials column beds filled within 100-800 mm, preferably within 250-600 mm.

In some specific embodiments of the present invention, the polyacrylate or polystyrene-divinyl benzene polymer microsphere has uniform diameter distribution and relatively low counterpressure, and is subjected to a separation and purification way of continuous flow chromatography.

The chromatographic conditions described in the present invention may be adjusted and changed to some extent in accordance with a general guidebook.

Some other conventional methods may be applied for dialysis, ultrafiltration and pasteurization steps for the chromatography described herein, which is free of affecting the implementation effectiveness of the present invention.

For the purification of recombinant human albumin, optionally, after the final completion of the chromatography described above, a membrane package of 100 KDa and/or 30 KDa and/or 10 KDa may be used to trap macromolecular aggregates and remove small molecules for continued purification, and the buffer solution is replaced and concentrated into a recombinant human albumin stock solution with a concentration greater than 20%. Alternatively, host cells expressing recombinant human protein include but are not limited to, yeasts, *Saccharomyces cerevisiae* containing saccharides *Saccharomyces* genus lineage, *Kluyveromyces* genus lineage, *Hansenula* genus lineage, and *Bichia* genus lineage.

Unless otherwise defined, all the technical and scientific terms used herein have the same meaning as commonly understood by those skilled in the art. In the event of conflict, it shall be subjected to the specification of this application. Preferred methods and materials are described below; methods and materials similar or equivalent to those described herein may be used to implement or test the present invention. The materials, methods, and examples disclosed herein are illustrative only and are not intended to be limiting.

Throughout this specification, the term "recombinant human albumin" may also be referred to as "recombinant human serum albumin" and/or "recombinant human blood albumin" and/or "rHA" and/or "rHSA". The term "human serum albumin" refers to human albumin extracted from human serum, which may also be referred to as "human blood albumin" and/or "HSA" and/or "HA" and/or "pdHSA".

Figure 1:
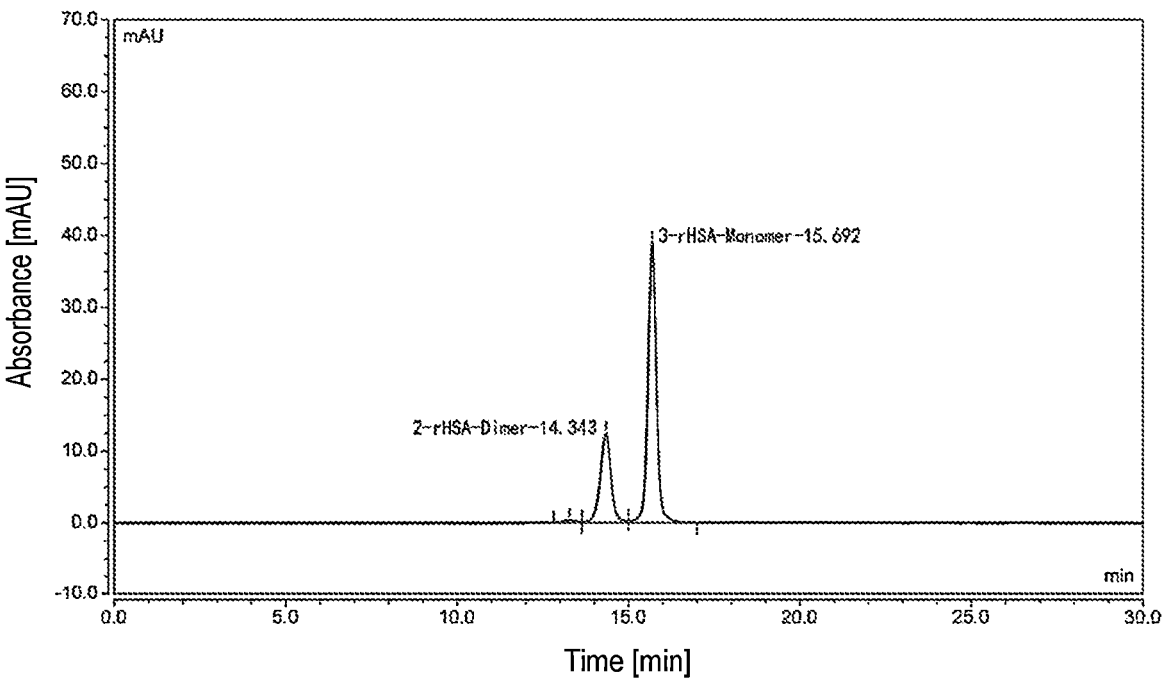
FIG. 1 illustrates the generation of polymers when the first step of enrichment purification is performed by a purification process without aminoguanidine.
Figure 2:
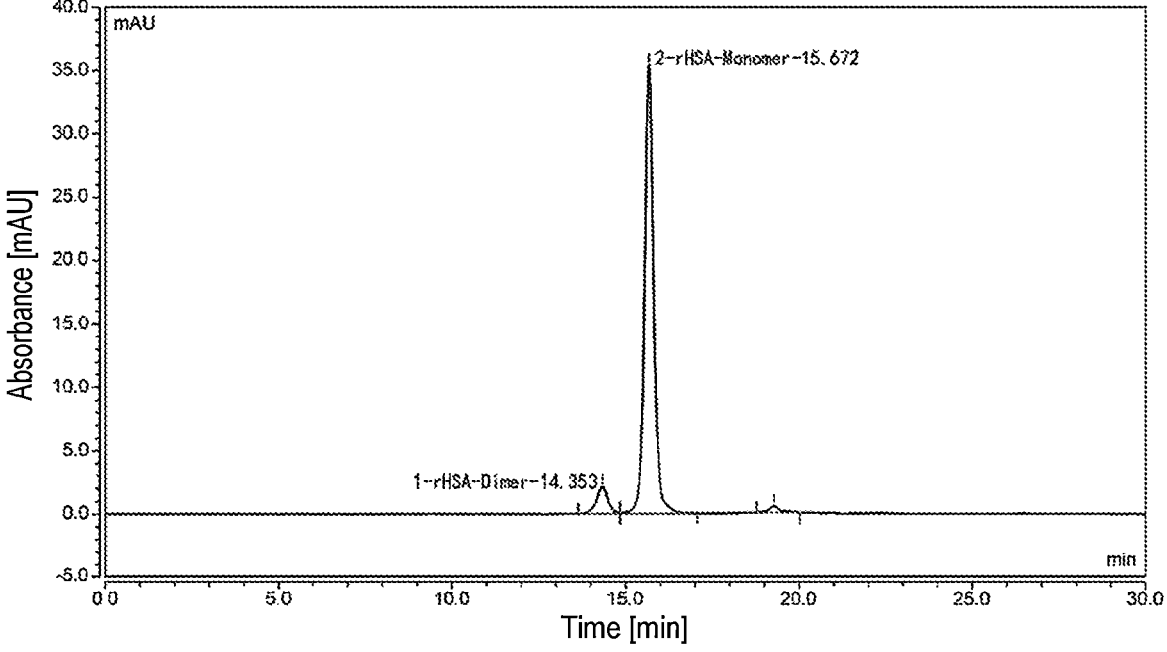
FIG. 2 illustrates addition of aminoguanidine to prevent and reduce the generation of dimers, polymers and heteromers according to a method of an embodiment of the present invention.
Figure 3:
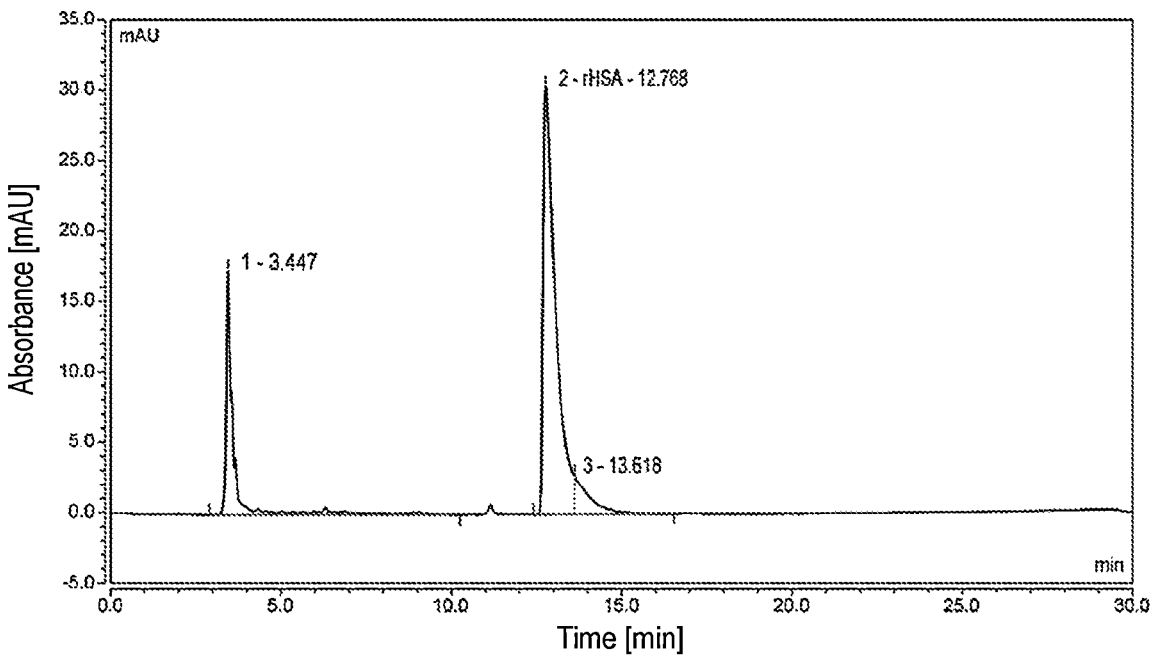
FIG. 3 illustrates a HPLC-C4 detection chromatogram of a collection solution in hydrophobic chromatography without adding a medium-long chain fatty acid.
Figure 4:
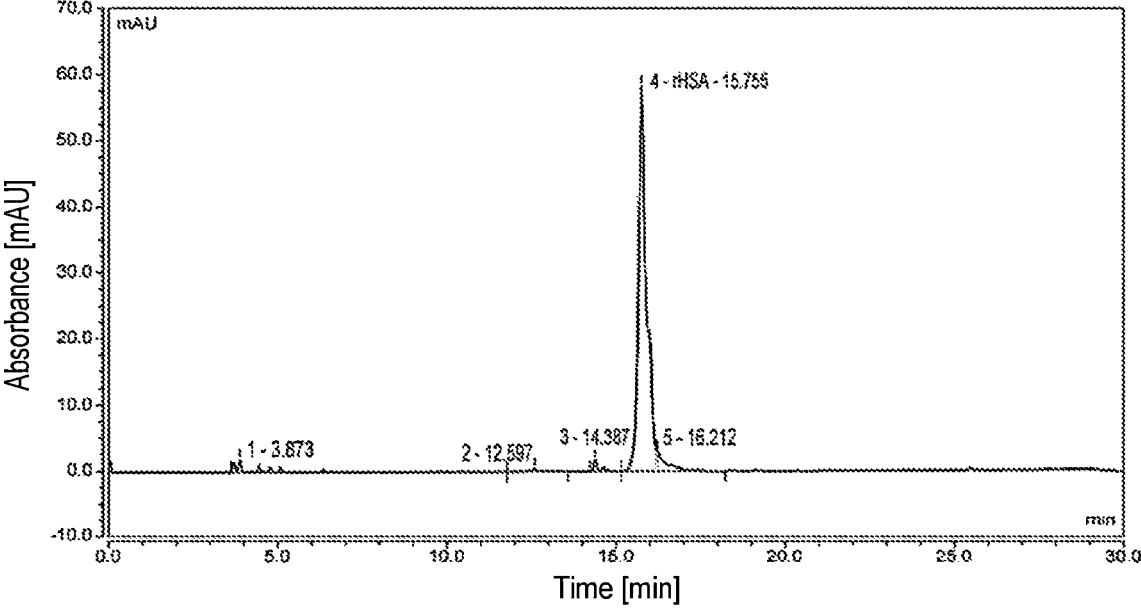
FIG. 4 illustrates a HPLC-C4 detection chromatogram of a collection solution in hydrophobic chromatography with a medium-long chain fatty acid, indicating the medium-long chain fatty acid acts as a strong active ligand to inhibit most of the host proteins, pigments and carbohydrates from interacting with albumin.

| 1 | Cation exchange chromatography collection solution | 0.2 ul |
| 2 | Hydrophobic chromatography loading flow-through-1 | 5 ul |
| 3 | Hydrophobic chromatography target collection solution-1 | 0.2 ul |
| 4 | Hydrophobic chromatography wash solution-1 | 1 ul |
| 5 | Hydrophobic chromatography cleansing solution-1 | 5 ul |
| 6 | Hydrophobic chromatography loading flow-through sample #1-2 | 5 ul |
| 7 | Hydrophobic chromatography loading flow-through sample #2-2 | 0.5 ul |
| 8 | Hydrophobic chromatography target collection solution-2 | 0.2 ul |
| 9 | Hydrophobic chromatography wash solution-2 | 2 ul |
| 10 | Hydrophobic chromatography cleansing solution-2 | 2 ul |

DETAILED DESCRIPTION OF THE EMBODIMENTS

The fermentation of the present invention was implemented on a scale of 10 L, 20 L, 3,000 L, and 10,0000 L equipment with good linear amplification at the purification scale of 10 cm, 45 cm, and 120 cm column diameters, respectively. The present embodiments include, but are not limited to, the above scales. The following embodiments in conjunction with the accompanying drawings provide further understanding of the features and advantages of the present invention but are not construed as limiting the remainder of the present invention in any way.

Example 1

Fermentation and Solid-Liquid Separation

The fermentation was performed according to the method of patent CN102190722 by constructing a strain of *Pichia pastoris* and an optimized medium and culture parameters, and after 300 hours of fermentation, 12 g/L fermentation broth of recombinant human albumin was obtained. The fermentation broth was centrifuged to separate the bacterial cells, and the supernatant was harvested, and then stabilizers were added and heated (sodium octanoate to a final concentration of 20 mM, aminoguanidine to a final concentration of 30 mM, cysteine to a final concentration of 10 mM and N-acetyltryptophan to a final concentration of 5 mM) at 64° C. for 60 minutes to inactivate the protease. After being filtered and clarified by a 0.22 μm hollow fiber membrane and washed with injection water, the solution was adjusted to a pH value of 4.0-4.5 with acetic acid.

The UniGel SP was loaded with a column bed height of 400 mm, the chromatography column was balanced with a balanced solution of 50 mM HAc+50 mM NaCl+10 mM aminoguanidine (pH=4.1), and the clarified and separated fermentation broth (containing 30 mmol/g sodium octanoate albumin) was loaded; the chromatography column was washed with the balanced solution; then the target protein was eluted with an elution buffer solution of 50 mM PB+170 mM NaCl+10 mM aminoguanidine (pH=8.3); after elution was completed, the medium was thoroughly cleaned and regenerated with 1 M NaCl+0.5 M NaOH solution and water.

Example 2

Hydrophobic Chromatography

The eluent collected in Example 1 was directly loaded onto a balanced hydrophobic chromatography column (UniHR Phenyl-80L, column bed height: 400 mm) with a balanced solution of 50 mM PB+160 mM NaCl pH 7.8+10 mM aminoguanidine, and the chromatography column was washed using the balanced solution, the sample containing recombinant human albumin was collected, and the medium was thoroughly cleaned and regenerated with 0.01 M NaOH and water.

Example 3

Removal of Aminoguanidine by Ultrafiltration

The protein solution collected in Example 2 was replaced with a 30 KDa and/or 10 KDa membrane package, thus removing aminoguanidine and other stabilizers, and purification was continued; and the solution was replaced and concentrated into a recombinant human albumin stock solution with a concentration greater than 20%.

Example 4

Figure 5:
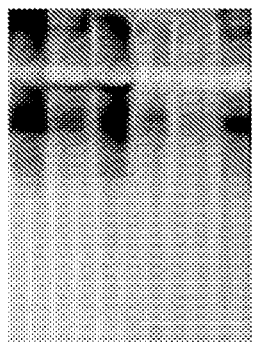
FIGS. 5 and 6 respectively show anti-HCP-Western Blotting reduction chromatogram and non-reduction chromatogram purified by two purification processes without and with aminoguanidine and a medium-long chain fatty acid according to the method of Example 4; lanes 1-6 represent a cation exchange collection solution-1, a cation exchange collection solution-3, a cation exchange collection solution-4, a cation exchange collection solution-5, a cation exchange collection solution-6 and a cation exchange collection solution-7, respectively (all loading volumes are 0.14 ul), where the numerical labels are purification process sub-batch numbers, −2 represents reserved samples for other experiments during the experimental process; −1/−3/−4 are samples produced by the production process without aminoguanidine, −4/−5/−6 are samples produced by the production process with the addition of aminoguanidine and a medium-long chain fatty acid according to the present invention.
Figure 6:
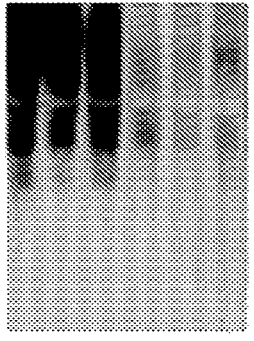
Figure 7:
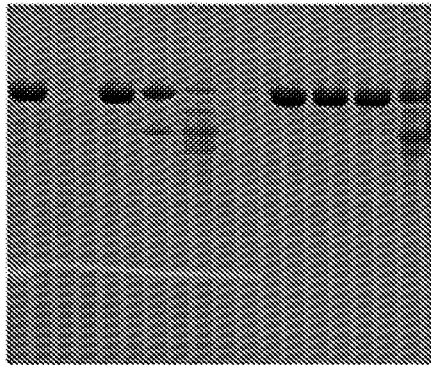
FIG. 7 illustrates a non-reducing electrophoresis SDS-PAGE chromatogram obtained from the comparative assay of the two purification processes using the same cation exchange chromatography collection solution according to the method of Example 4; in this experiment, the same batch of cation exchange chromatography collection solution is taken and the protein is purified accordingly using two purification processes containing aminoguanidine and a medium-long chain fatty acid and free of aminoguanidine and a medium-long chain fatty acid, and the generation of polymers is compared; −1 represents the sample purified by the purification production process without aminoguanidine and a medium-long chain fatty acid; 2 represents the sample purified by the production process with the addition of aminoguanidine and a medium-long chain fatty acid according to the present invention; sample loading conditions of the lanes 1-10 are as follows.

Comparison of the Purification Process of the Present Invention and the Purification Process without Aminoguanidine and a Medium-Long Chain Fatty Acid The fermentation broth produced by the same fermentation process was purified under the purification conditions without the addition of aminoguanidine and a medium-long chain fatty acid; the purification was performed under the conditions of adding aminoguanidine and sodium oleate according to the methods of Example 1 and Example 2 of the present invention. There are obvious differences through the comparison of the purification effect, the comparison of liquid chromatography assay (FIG. 1, FIG. 2, FIG. 3, and FIG. 4), the comparison of electrophoresis detection (FIG. 5, FIG. 6, and FIG. 7), and the comparison of sugar detection results (Table 1).

and sodium hydroxide were added to precipitate the protein, after centrifugation at 8000 rpm for 15 minutes, supernatant was absorbed into a 96-well plate, then freshly prepared acetylacetone-ammonium acetate mixture was added, and the 96-well plate was incubated at 37° C. for 1 hour. The sugar content was calculated by colorimetric analysis at a wavelength of 405 nm on a fully automatic microplate reader.

Although certain features of the present invention have been explained and described herein, many modifications,

TABLE 1

| | Process flow detection without aminoguanidine and a medium-long chain fatty acid (glycoprotein ug/mg protein) | | | Process flow detection in the present invention (glycoprotein ug/mg protein) | |
|---|---|---|---|---|---|
| Loading stock solution | Total solution collected by cation exchange chromatography | Total solution collected by hydrophobic chromatography | Loading stock solution | Total solution collected by cation exchange chromatography | Total solution collected by hydrophobic chromatography |
| 341.09 | 5 | 1.04 | 358.96 | 0.4 | 0.17 |
| 224.02 | 5.19 | 1.06 | Undetected | 0.29 | 0.21 |
| 343.11 | 5.37 | 1.11 | 317.24 | 0.42 | Undetected |

Example 5

Detection Method for Quality Control Items During Protein Purification

1. HPLC detection method: the main detection method for chromatography 1 was HPLC-SEC detection method/HPLC-C4 detection method:

detection method: the corresponding detection method was established by referring to 3121 A Method for Determining Human Blood Albumin Polymers, General Rules, Volume III of the *Pharmacopoeia of People's Republic of China,* 2015 edition, thus measuring the polymers (including polymers and dimers) in the recombinant human albumin solution;

detection method: the corresponding detection method was established by referring to the 0512 High Performance Liquid Chromatography, General Rules, Volume III of the *Pharmacopoeia of People's Republic of China,* 2015 edition, thus measuring the pigment-binding proteins and partial sugar-binding proteins in the recombinant human albumin solution.

2. Electrophoresis detection method: the main detection method for hydrophobic chromatography was SDS-polyacrylamide gel electrophoresis:

detection method: sample detection was performed by referring to (0541 Method Five SDS-Polyacrylamide Gel Electrophoresis, General Rule), Volume IV of the *Pharmacopoeia of People's Republic of China,* 2015 edition;

relevant sample detection was performed by referring to (3401 Western Blotting, General Rule), Volume IV of the *Pharmacopoeia of People's Republic of China,* 2015 edition.

3. Detection of sugar content by PAS method:

Test solution was taken and added to hydrochloric acid solution to make the solution pH acidic, and sodium periodate was added and mixed thoroughly, the cis-ethylene glycol group in the polysaccharide was oxidized in the test sample to aldehyde at room temperature, and then the reaction was terminated by an ice bath, and ice zinc sulfate substitutions, alterations, and equivalents will be envisaged by those skilled in the art. Accordingly, it is to be understood that the appended claims are intended to cover all such modifications and alterations falling within the scope of the true spirit of the present invention.

What is claimed is:

1. A method for purification of a recombinant protein, comprising:

(a) adding aminoguanidine and a medium-long chain fatty acid to a sample containing the recombinant protein; and (b) chromatographing the obtained sample, wherein the chromatography is optionally performed with a chromatographic buffer solution containing aminoguanidine, wherein the chromatography comprises cation exchange chromatography and hydrophobic chromatography, and wherein aminoguanidine in a chromatographic balanced solution, a wash solution or an elution buffer solution for the cation exchange chromatography has a concentration of 1-200 mmol/L.

2. The method according to claim 1, wherein the aminoguanidine in the step (a) has a concentration of 2-100 mmol/g (recombinant protein).

3. The method according to claim 1, wherein the medium-long chain fatty acid is selected from one or more of octanoic acid, capric acid, myristic acid (C14:0), palmitic acid (C16:0), stearic acid (C18:0), oleic acid (C18:1), linoleic acid (C18:2), linolenic acid (C18:3), arachidonic acid (C20:4) and a salt thereof.

4. The method according to claim 1, wherein the medium-long chain fatty acid has a concentration of 2-300 mmol/g (recombinant protein).

5. The method according to claim 1, wherein the chromatographic balanced solution and the wash solution for the cation exchange chromatography have a pH value of 4.0-6.0; the elution buffer solution has a pH value of 7.0-9.5.

6. The method according to claim 1, wherein the chromatographic balanced solution and the wash solution for the cation exchange chromatography have a conductivity not greater than 15 ms/cm; the elution buffer solution has a conductivity not greater than 30 ms/cm.

7. The method according to claim 1, wherein the chromatographic balanced solution and the wash solution for the cation exchange chromatography are phosphoric acid, acetic acid or a Tris buffer solution.

8. The method according to claim 1, wherein a medium substrate for the cation exchange chromatography is selected from a polyacrylate substrate, a polystyrene-divinyl benzene substrate, an agarose substrate, and a modified cellulose substrate; wherein the polyacrylate substrate is a hydrophilic modified polyacrylate.

9. The method according to claim 1, wherein a medium for the cation exchange chromatography is coupled with a hydrophobic cationic ligand, and the hydrophobic cationic ligand comprises a highly salt tolerant Sepharose Capto MMC.

10. The method according to claim 1, wherein a medium for the hydrophobic chromatography is hydrophilically modified agarose, polyacrylate, polystyrene-divinyl benzene substrate microspheres coupled with a hydrophobic ligand of Phenyl or Butyl series; or a medium for the hydrophobic chromatography is a hydrophilic polymethacrylate matrix coupled with a hydrophobic ligand of Phenyl or Butyl series.

11. The method according to claim 1, wherein the hydrophobic chromatography has a pH value of 6.0-8.5.

12. The method according to claim 1, wherein the hydrophobic chromatography has a conductivity not greater than 30 ms/cm.

13. The method according to claim 1, wherein aminoguanidine in a loading solution for the hydrophobic chromatography has a concentration of 1-100 mmol/g recombinant protein.

14. The method according to claim 1, wherein the aminoguanidine is in a form of salt thereof.

15. The method according to claim 1, wherein the recombinant protein is a recombinant human albumin.

16. The method according to claim 1, wherein the recombinant protein is G-CSF, GLP-1, interferon, growth hormone, interleukin and analogues thereof, and fusion proteins of the above proteins with albumin; and/or the sample containing the recombinant protein is a fermentation supernatant.

* * * * *